(12) United States Patent (10) Patent No.: US 12,428,761 B2
Oslund et al. (45) Date of Patent: Sep. 30, 2025

(54) BRAIDED MEDICAL DEVICE AND METHOD

(71) Applicant: KA Medical, LLC, Roseville, MN (US)

(72) Inventors: John Oslund, Blaine, MN (US); Pat Russo, Vadnais Heights, MN (US); Kevin Dunne, St. Paul, MN (US)

(73) Assignee: KA Medical, LLC, Roseville, MN (US)

( * ) Notice: Subject to any disclaimer, the term of this patent is extended or adjusted under 35 U.S.C. 154(b) by 0 days.

(21) Appl. No.: 18/436,639

(22) Filed: Feb. 8, 2024

(65) Prior Publication Data

US 2024/0263370 A1 Aug. 8, 2024

Related U.S. Application Data

(62) Division of application No. 17/198,014, filed on Mar. 10, 2021, now Pat. No. 11,932,976.

(60) Provisional application No. 62/988,100, filed on Mar. 11, 2020.

(51) Int. Cl.
*D04C 1/02* (2006.01)
*D04C 1/06* (2006.01)
*D04C 3/40* (2006.01)
*A61M 25/09* (2006.01)

(52) U.S. Cl.
CPC ............... *D04C 1/02* (2013.01); *D04C 1/06* (2013.01); *D04C 3/40* (2013.01); *A61M 2025/09141* (2013.01)

(58) Field of Classification Search
CPC ... D04C 1/02; D04C 1/06; D04C 3/40; A61M 2025/09141; A61F 2250/0039
See application file for complete search history.

(56) References Cited

U.S. PATENT DOCUMENTS

| 5,419,231 | A | 5/1995 | Earle et al. |
| 5,899,134 | A | 5/1999 | Klein et al. |
| 8,261,648 | B1 | 9/2012 | Marchand et al. |
| 8,850,942 | B2 | 10/2014 | Masson et al. |

(Continued)

FOREIGN PATENT DOCUMENTS

| WO | 2015117148 | 8/2015 |
| WO | 2017214431 | 12/2017 |

OTHER PUBLICATIONS

International Search Report and Written Opinion dated Jun. 30, 2021 for PCT/US2021/021760.

(Continued)

*Primary Examiner* — Shaun R Hurley
(74) *Attorney, Agent, or Firm* — Dorsey & Whitney LLP

(57) ABSTRACT

A method for making a neutral hybrid braided structure may involve positioning a first set of wires on a braiding machine in a first set of positions, positioning a second set of wires on the braiding machine in a second set of positions so that the first set of positions and the second set of positions form a neutral hybrid braiding pattern, and braiding the first set of wires and the second set of wires on the braiding machine to form the neutral hybrid braided structure. Each wire in the first set of wires has a first cross-sectional diameter, and each wire in the second set of wires has a second cross-sectional diameter that is smaller than the first cross-sectional diameter.

15 Claims, 7 Drawing Sheets

(56) References Cited

U.S. PATENT DOCUMENTS

| | | |
|---|---|---|
| 9,265,633 B2 | 2/2016 | Palasis et al. |
| 2013/0092013 A1 | 4/2013 | Thompson et al. |
| 2013/0211492 A1 | 8/2013 | Schneider et al. |
| 2014/0100644 A1 | 4/2014 | Palasis et al. |
| 2016/0120570 A1 | 5/2016 | Kobayashi et al. |
| 2016/0168769 A1 | 6/2016 | McDonnell |
| 2016/0345674 A1 | 12/2016 | Bruce et al. |
| 2017/0354402 A1 | 12/2017 | Lee et al. |
| 2019/0223879 A1 | 7/2019 | Jayaraman |
| 2019/0374228 A1* | 12/2019 | Wallace ............ A61B 17/1214 |

OTHER PUBLICATIONS

Notice of Allowance dated Dec. 5, 2023 for U.S. Appl. No. 17/198,014.

Office Action dated Aug. 9, 2023 for U.S. Appl. No. 17/198,014.

* cited by examiner

| Neutral Hybrid - Braider Setup |||||||
|---|---|---|---|---|---|
| Carrier | Direction | Wire Size | Carrier | Direction | Wire Size |
| 1 | CCW | Large | 37 | CCW | Large |
| 2 | CW | | 38 | CW | |
| 3 | CCW | Small | 39 | CCW | Small |
| 4 | CW | | 40 | CW | |
| 5 | CCW | Large | 41 | CCW | Large |
| 6 | CW | | 42 | CW | |
| 7 | CCW | | 43 | CCW | |
| 8 | CW | Small | 44 | CW | Small |
| 9 | CCW | | 45 | CCW | |
| 10 | CW | Large | 46 | CW | Large |
| 11 | CCW | | 47 | CCW | |
| 12 | CW | Small | 48 | CW | Small |
| 13 | CCW | | 49 | CCW | |
| 14 | CW | Large | 50 | CW | Large |
| 15 | CCW | | 51 | CCW | |
| 16 | CW | Small | 52 | CW | Small |
| 17 | CCW | | 53 | CCW | |
| 18 | CW | Large | 54 | CW | Large |
| 19 | CCW | | 55 | CCW | |
| 20 | CW | | 56 | CW | |
| 21 | CCW | | 57 | CCW | |
| 22 | CW | Small | 58 | CW | Small |
| 23 | CCW | | 59 | CCW | |
| 24 | CW | Large | 60 | CW | Large |
| 25 | CCW | | 61 | CCW | |
| 26 | CW | Small | 62 | CW | Small |
| 27 | CCW | | 63 | CCW | |
| 28 | CW | Large | 64 | CW | Large |
| 29 | CCW | | 65 | CCW | |
| 30 | CW | Small | 66 | CW | Small |
| 31 | CCW | | 67 | CCW | |
| 32 | CW | Large | 68 | CW | Large |
| 33 | CCW | | 69 | CCW | |
| 34 | CW | Small | 70 | CW | Small |
| 35 | CCW | | 71 | CCW | |
| 36 | CW | | 72 | CW | |

*FIG. 5*

BRAIDED MEDICAL DEVICE AND METHOD

RELATED APPLICATIONS

The present application is a divisional of U.S. patent application Ser. No. 17/198,014 filed on Mar. 10, 2021, titled, 'BRAIDED MEDICAL DEVICE AND METHOD', which claims priority to U.S. Provisional Application No. 62/988,100, filed on Mar. 11, 2020 and titled, "BRAIDED MEDICAL DEVICE AND METHOD," which are both hereby incorporated by reference in their entireties.

TECHNICAL FIELD

The present application is related to medical devices and methods. More specifically, the application is related to braided medical devices and methods for manufacturing them.

BRIEF DESCRIPTION OF THE DRAWINGS

FIG. 5 is a table illustrating the neutral hybrid braid pattern set-up of FIG. 4A

DETAILED DESCRIPTION

Figure 1:
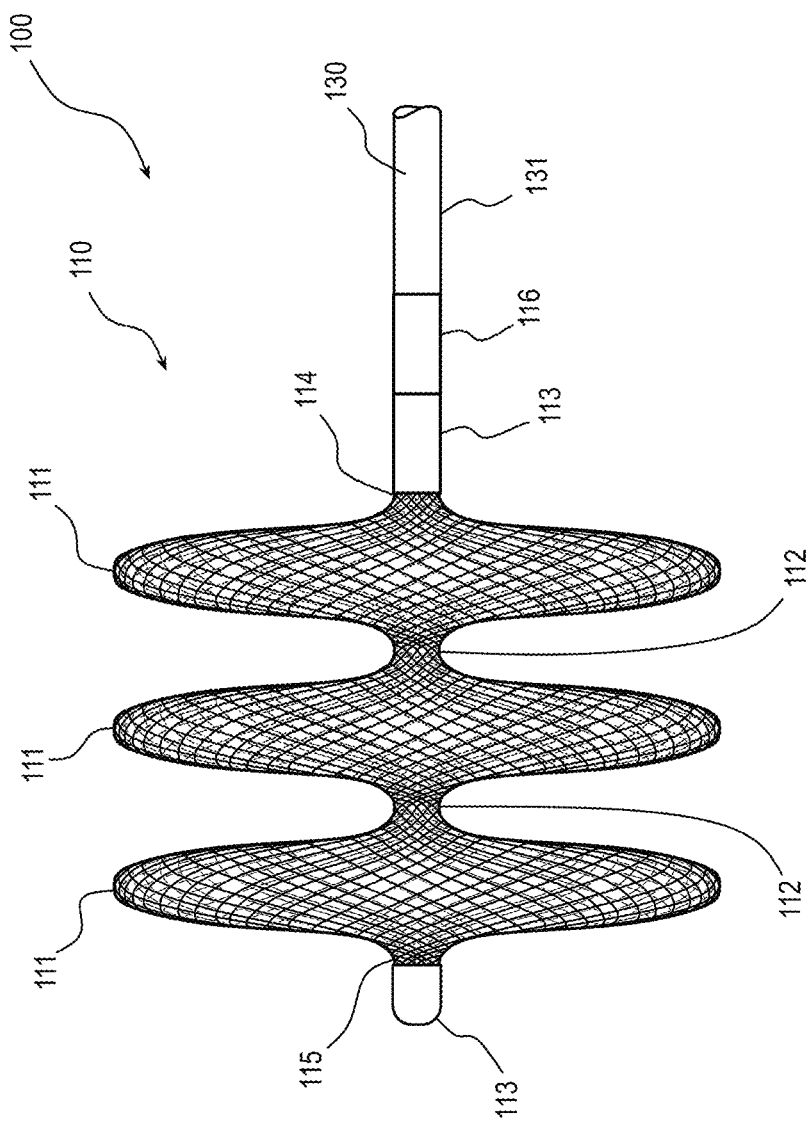
FIG. 1 is a side view of an embodiment of an expanding medical device in an expanded configuration.

Braided medical devices are used for a number of different applications in the body. In certain instances, implantable braided devices are used in vascular and cardiovascular procedures to prop open a blood vessel, act as a filter for capturing blood clots, occlude a blood vessel, occlude a congenital or structural cardiac defect, act as a support structure for an artificial valve, and the like. In some embodiments, a braided device is delivered to its implant location in the body through a catheter in a collapsed, smaller diameter configuration and then, after exiting the catheter, it expands into a larger diameter configuration to contact and attach itself to the wall of the blood vessel or other lumen or defect in which it is being implanted.

Braided devices can be made of multiple wires, including wires made of a shape memory material, such as Nitinol, braided together to form the structure of the device. Some braided devices use wires that are all the same material and the same diameter. In other devices, wires with different diameters are used (a process called "hybrid braiding"), to create a device. Some reasons for using hybrid braiding include:

(a) to create a device with a desired overall stiffness (if using all larger wires would be too stiff and using all smaller wires would be too flexible); (b) to create a device with a desired cross-sectional area (if using all larger wires would be too large and using all smaller wires would be too small); and (c) no single wire size will provide the desired properties for the given braided device.

Braided devices work well in many applications, but they can sometimes cause technical challenges or issues. For example, a hybrid braided device can sometimes experience unintentional rotation when moved through a lumen of a delivery catheter or other delivery device, due to the helical nature of the braid or a helical bias created by using wires of different sizes. This may be problematic if the device being moved through the lumen is connected to a delivery member by means of a screw thread. If the threaded connection is a clockwise (CW) direction and the braided device experiences rotation in the opposite direction when moved, then the device could unscrew from the member before it is delivered to its intended location or deploy in an uncontrolled manner. Conversely, if the threaded connection is a counterclockwise (CCW) direction and the braided device experiences rotation in the same direction when moved, then the threaded connection could bind, thus preventing detachment of the device from the member. The unintentional rotation may also cause scraping and/or abrasion of the lumen the device is being moved through.

In another example, when a hybrid braided device and the device used for delivering it in the body are permanently connected to one another (glued, welded, brazed, etc.), unintentional rotation of the hybrid braided device relative to the delivery device may cause torque loads leading to deformation and/or failure of the braided structure and/or of the connected delivery member.

An embodiment of a hybrid braided device disclosed within the scope of this application includes a first set of wires arranged in a first set of positions and a second set of wires arranged in a second set of positions, wherein the first set of wires and the second set of wires are braided together to form a neutral hybrid braided device. In some embodiments, a diameter of each of the first set of wires is greater than a diameter of each of the second set of wires. The hybrid braided device may further include a plurality of CW high points where the second set of wires cross over the first set of wires in a CW direction and a plurality of CCW high points where the second set of wires cross over the first set of wires in a CCW direction.

A method of braiding the hybrid braided device disclosed within the scope of this application includes positioning the first set of wires on a braiding machine in a first set of positions, positioning a second set of wires on the braiding machine in a second set of positions, and braiding the first set of wires and the second set of wires on the braiding machine to form a hybrid braided device having a neutral hybrid braided pattern.

A method of deploying the hybrid braided device disclosed within the scope of this application includes the steps of rotationally coupling the hybrid braided device to a placement wire, disposing the braided wire structure within a lumen of a delivery catheter, wherein the braided wire structure is radially constrained; moving the constrained device axially through the inner lumen of the catheter to a target location within the patient; and minimizing or preventing rotation of the hybrid braided device relative to the placement wire. The prevention or limiting of the rotation of the hybrid braided device is facilitated by a plurality of CW high points and a plurality of CCW high points of the hybrid braided device to counteract one another during axial movement.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Figure 2:
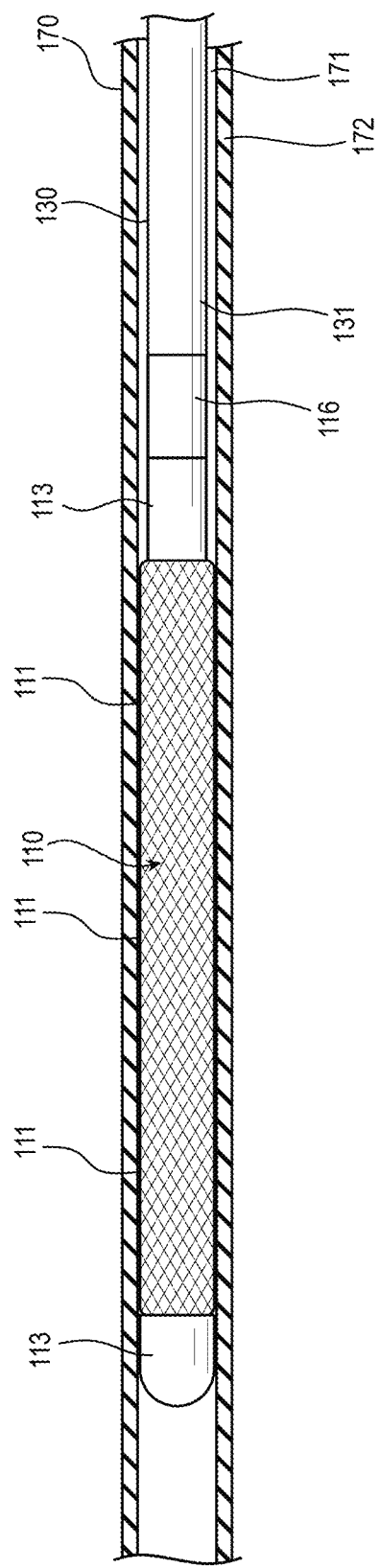
FIG. 2 is a side view of the expanding medical device of FIG. 1 in a constrained configuration.
Figure 3A:
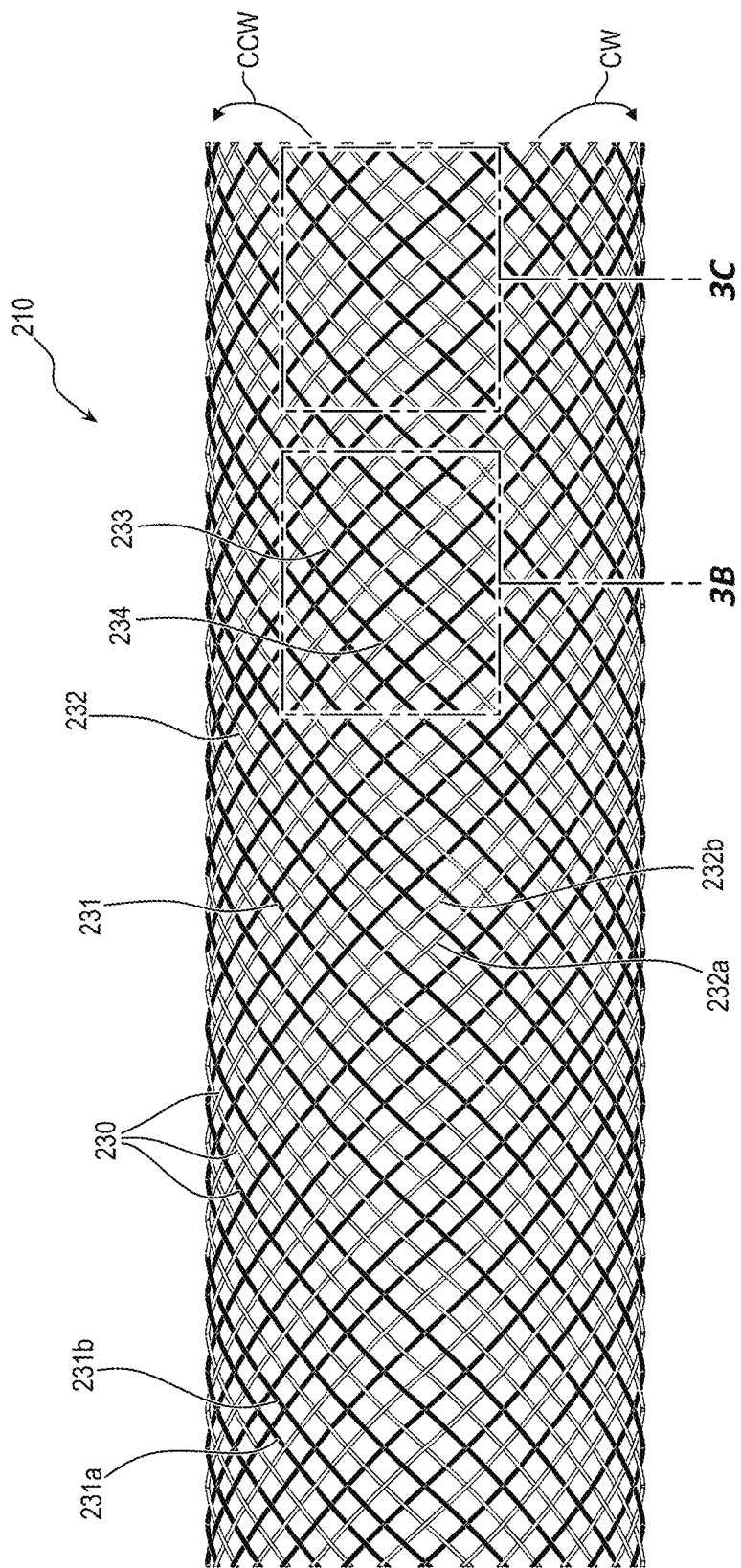
FIG. 3A is a side view of an embodiment of a braided wire structure of the expanding medical device of FIG. 1 including the neutral hybrid braid pattern.
Figure 3B:
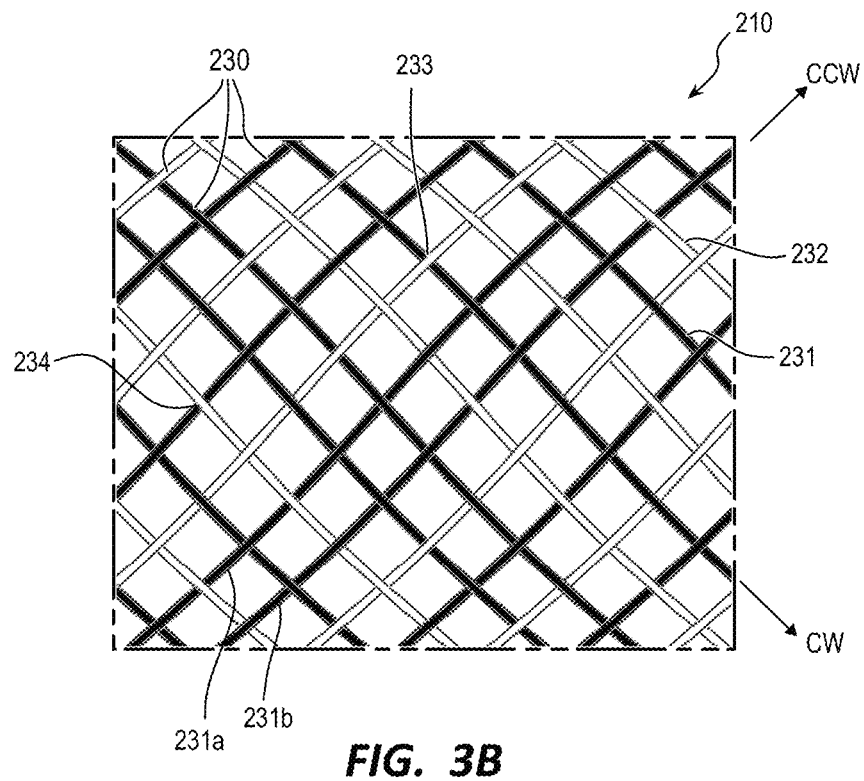
FIG. 3B is a close-up view of a portion of the braided wire structure of FIG. 3A.
Figure 3C:
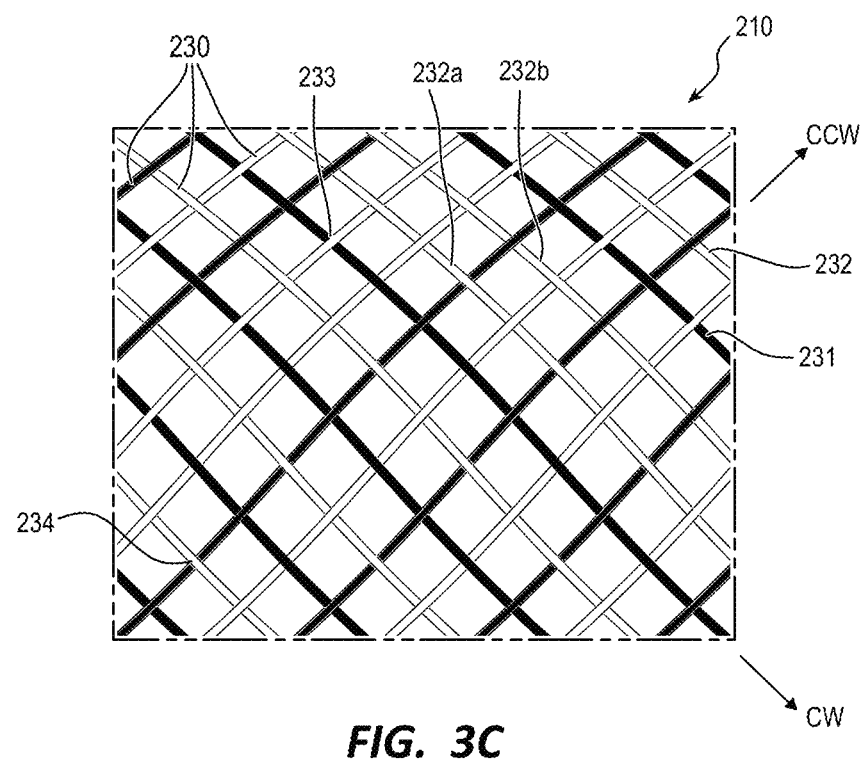
FIG. 3C is another close-up view of a portion of the braided wire structure of FIG. 3A.
Figure 4A:
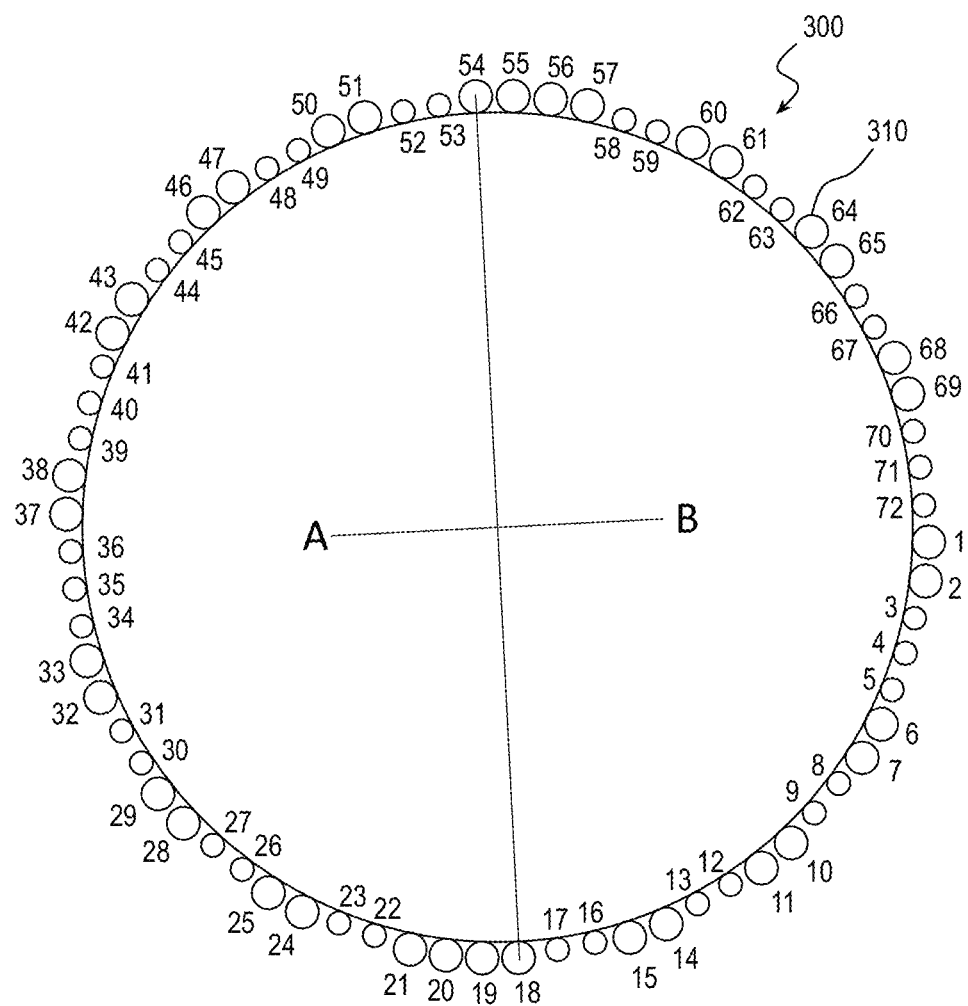
FIG. 4A is a schematic front view of an embodiment of a wire braiding machine showing a set-up for a neutral hybrid braid pattern.
Figure 4B:
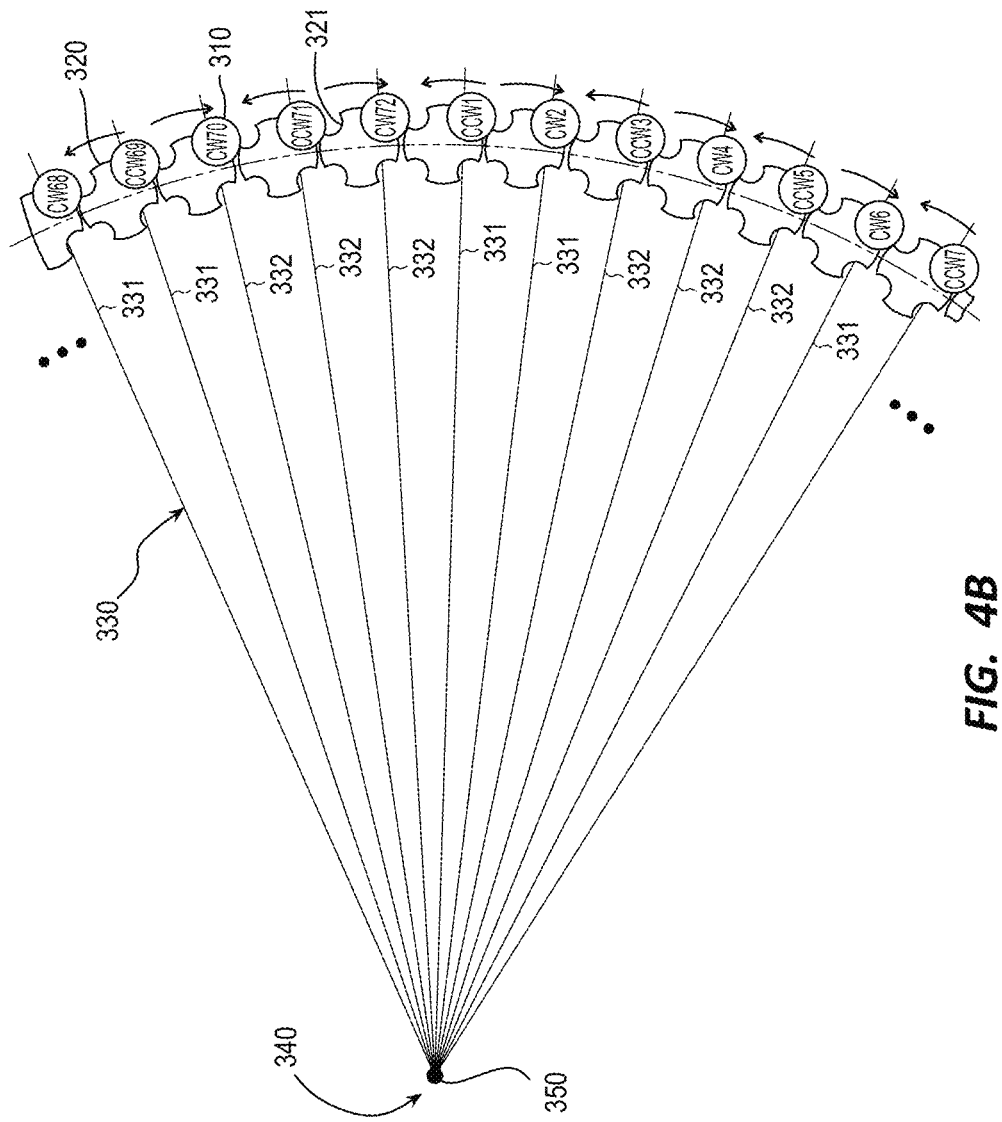
FIG. 4B is a schematic side view of a portion of the wire braiding machine of FIG. 4A.

FIG. 1 illustrates an embodiment of an expanding medical device in an expanded configuration. FIG. 2 illustrates the expanding medical device in a constrained configuration. FIGS. 3A-3C illustrate an embodiment of a braided wire structure of the expanding medical device including the neutral hybrid braid pattern. FIGS. 4A, 4B, and 5 illustrate an embodiment of a wire braiding machine showing a set-up for a neutral hybrid braid pattern. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIG. 1 depicts an embodiment of an expanding device 100 in an expanded state. In the embodiment illustrated in FIG. 1, the expanding device 100 includes a neutral hybrid braided wire structure 110. The neutral hybrid braided wire structure 110 is composed of three lobes or segments 111 with reduced diameter portions 112 disposed between the lobes 111. In another embodiment, the neutral hybrid braided wire structure 110 may include a single lobe 111. In yet another embodiment, the neutral hybrid braided wire structure 110 may include two lobes 111 with a reduced diameter portion 112 disposed between the two lobes 111. Embodiments with more than three lobes 111, including embodiments with four, five, six, or more lobes 111, are likewise within the scope of this disclosure. In the illustrated embodiment, in the expanded state, the lobes 111 have a disc shape. Embodiments where the expanded shape is spherical, ovoid, cylindrical, or any other shape and where the expanded shapes may vary within an expanding device 100 are likewise within the scope of this disclosure.

In the illustrated embodiment, the neutral hybrid braided wire structure 110 includes a woven lattice or matrix of wires made from any suitable material and may be self-expanding. For example, the material may be Nitinol or any other suitable shape memory metal or polymer or any braidable material. In other embodiments, the woven lattice may be balloon-expandable and may be made from any suitable material, such as stainless steel, titanium, etc. The ends of the wires can be restrained by clamps 113 disposed at the proximal end 114 and the distal end 115 to prevent fraying of the braid. The neutral hybrid braided wire structure 110 can be releasably coupled to a placement wire 130 for deployment. For example, in the illustrated embodiment the neutral hybrid braided wire structure 110 includes a threaded coupling 116 disposed at the proximal end 114 that can be threadingly coupled to a threaded coupling 131 of the placement wire 130. When deployed, the neutral hybrid braided wire structure 110 can be rotationally held in place relative to the placement wire 130 when the neutral hybrid braided wire structure 110 engages with the vessel wall and the placement wire 130 can be rotated to release the placement wire 130 from the neutral hybrid braided wire structure 110. Other mechanisms for release and deployment are also within the scope of this disclosure including, hooks, collets, loops, snares, and so forth.

FIG. 2 illustrates the expanding device 100 in a radially collapsed or constrained or low-profile state. As illustrated, the expanding device 100 is disposed within a lumen 171 of a delivery device 170 (e.g., delivery catheter). The neutral hybrid braided wire structure 110 is radially compressed and constrained by a wall 172 of the delivery device 170 wherein the lobes 111 are in contact with the wall 172 resulting in frictional resistance as the neutral hybrid braided wire structure 110 is pushed through the delivery device 170. In the constrained state, the neutral hybrid braided wire structure 110 is axially lengthened relative to the length of the neutral hybrid braided wire structure 110 in the expanded state, as shown in FIG. 1.

FIGS. 3A-3C illustrate a neutral hybrid braided wire structure 210. As illustrated, the neutral hybrid braided wire structure 210 includes wires 230 braided together in a neutral hybrid braid pattern. The wires 230 can be formed from any suitable material. For example, in an embodiment, the wires 230 are formed from a shape memory alloy, such as nickel-titanium alloy. In some embodiments, the material is Nitinol. In another embodiment, the wires 230 are formed from any one of stainless steel and titanium. Other suitable materials are contemplated. A diameter of the wires 130 can range from about 0.0005 inches to about 0.010 inches. In the embodiment disclosed by this disclosure, the wires include a combination of large wires 231 and small wires 232. A diameter of the large wires 231 may range from about 0.0005 inches to about 0.010 inches and a diameter of the small wires 232 may range from about 0.0005 inches to about 0.008 inches. When a combination of large wires 231 and small wires 232 are braided together, various physical characteristics of the neutral hybrid braided wire structure 110 may be provided. The physical characteristics can include stiffness, flexibility, compressibility, radial expansion, profile, diameter, etc. For example, the stiffness of the neutral hybrid braided wire structure 210 is higher when a wire braid includes both large wires 231 and small wires 232 when compared to a braided wire structure composed strictly of small wires.

In the illustrated embodiment, the neutral hybrid braided wire structure 210 includes localized areas where pairs of large wires 231a, 231b, as shown in FIG. 3B, and pairs of small wires 232a, 232b, as shown in FIG. 3C, travel in both the CW and CCW directions. There are two CW-travelling large wire pairs and two CCW-travelling large wire pairs and two CW-travelling small wire pairs and two CCW-travelling small wire pairs. The wires 230 are braided in an over-under-over pattern. For example, a first wire is braided over a second wire traveling perpendicularly to the first wire, under a third wire traveling parallel to the second wire, and over a fourth wire traveling parallel to the third wire. In other embodiments, the wires 230 may be braided in any suitable pattern. For example, the wires 230 may be braided in an over two-under one-over two pattern.

As illustrated, the large wires 231 and the small wires 232 travel in both a CW direction and a CCW direction. The small wires 232 overlap the perpendicularly traveling large wires 231 in the CCW direction and in the CW direction to form CCW high points 233 and CW high points 234. When the neutral hybrid braided wire structure 210 is constrained within a lumen of a delivery catheter, wherein the CCW high points 233 and the CW high points 234 engage with a wall of the lumen, and is either pulled proximally (toward the user) or pushed distally (away from the user) through the lumen of the delivery catheter, a rotation of the neutral hybrid braided wire structure 210 will be neutral. In other words, the CCW high points 233 and CW high points 234 will counteract each other to resist or prevent the neutral hybrid braided wire structure 210 from rotating either CW or CCW. This prevents or minimizes the neutral hybrid braided wire structure 210 from either inadvertently detaching from a placement wire within the delivery catheter or tightening onto the placement wire to prevent intended rotational detachment of the neutral hybrid braided wire structure 210 from the placement wire within a blood vessel.

The neutral hybrid braided wire structure 210 can be formed by a wire braiding machine. FIG. 4A illustrates a partial front schematic view of a 144 carrier wire braiding machine 300. In other embodiments, the wire braiding machine 300 may be a 32 carrier, 96 carrier, or any number of carries wire braiding machine. The wire braiding machine 300 is shown in a "Half Load" configuration, where only 72 of the possible 144 wire carriers 310 are present on the wire braiding machine 300. Thirty-six of the wire carriers 310 are configured to travel CW around the wire braiding machine 300, and the other 36 wire carriers 310 are configured to travel CCW around the wire braiding machine 300. The wire carriers 310 are selectively coupled to horn gears 320, as shown in FIG. 4B. The horn gears 320 rotate about their own central axis and pass each wire carrier 310 from one horn gear 320 to an adjacent horn gear 320. A rotation direction of a first horn gear 320 is opposite to a rotation direction of an adjacent second horn gear 320 and so on, as shown by the arrows of FIG. 4B. In other words, the first horn gear 320 may rotate CW and the immediate adjacent second horn gear 320 may rotate CCW. Notches 321 in the horn gears 320 are configured to hold the wire carriers 310 until they are passed to the next horn gear 320. Each wire carrier 310 holds a single wire spool (not shown). The wire carriers 310 are loaded with wires 330 in a specific order to achieve the neutral braided wire pattern. The wires 330 all converge at a central point onto a mandrel 340 to form a neutral hybrid braid 350 from which a neutral hybrid braided wire structure is formed.

Each wire 330 makes 360-degree rotations around the mandrel 340. A length of the neutral hybrid braid 350 produced on each mandrel 340 can be multiple feet, meaning that each wire 330 makes multiple 360-degree rotations around the mandrel 340. The amount of the neutral hybrid braid 350 required to produce an expanding device may be a fraction of what is produced on each mandrel 340, so the braiding process can be a bulk production process.

FIG. 4A illustrates a set-up of the wire braiding machine 300 to form the neutral hybrid braid 350 including the neutral hybrid braid pattern according to one embodiment within the scope of this disclosure. The set-up of the braiding machine 300 begins with loading a large wire spool onto the CCW direction travelling carrier #1. Then, another large wire spool is loaded onto the CW direction travelling carrier #2. Next, three small wire spools are loaded onto the next three carriers (#4, #5, #6). The localized groupings of small 332 and large wires 331 are arranged per the table of FIG. 5, which states the location, size, and direction for each of the 72 wires 330. The wire loading process continues until a total of 36 small wire spools and 36 large wire spools are loaded onto the carriers 310, with an equal amount of large and small wire spools travelling in both the CW and CCW directions.

The set-up of the braiding machine 300 for the neutral hybrid braid pattern is symmetrical, even with the inclusion of localized groupings of large and small wires spools. When a straight line is drawn from any carrier 310 through the center of the braiding machine 300, it will connect to another carrier 310 that has the same wire size spool and is travelling in the same direction. For example, carrier #18 has a large wire spool, carrier #54 has a large wire spool, and both are travelling CW, as shown in FIG. 4A. Therefore, carrier #18 is the 180-degree mirror image of carrier #54 about the line A-B. The symmetry or mirroring applies to all carriers 310 on the braiding machine 300.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified. For example, a method of deploying an expanding medical device may include one or more of the following steps: rotationally coupling a braided wire structure to a placement wire, wherein the braided wire structure comprises: a plurality of CW high points and a plurality of CCW high points; disposing the braided wire structure within a lumen of a delivery catheter, wherein the braided wire structure is radially constrained; moving the constrained device axially through the inner lumen of the catheter to a target location within the patient; and preventing or limiting rotation of the braided wire structure relative to the placement wire. Other steps are also contemplated.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment.

The phrase "coupled to" refers to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest to the practitioner during use. As specifically applied to an expanding medical device of this disclosure, the proximal end of the device refers to the end nearest to the practitioner and the distal end refers to the opposite end, the end furthest from the practitioner.

References to approximations are made throughout this specification, such as by use of the term "about." For each such reference, it is to be understood that, in some embodiments, the value, feature, or characteristic may be specified without approximation. For example, where the qualifier such as "about" is used, these terms include within their scope the qualified words in the absence of their qualifiers.

The terms "a" and "an" can be described as one, but not limited to one. For example, although the disclosure may recite a braided structure having "a wire," the disclosure also contemplates the braided structure having two or more wires.

Unless otherwise stated, all ranges include both endpoints and all numbers between the endpoints.

Recitation in the claims of the term "first" with respect to a feature or element does not necessarily imply the existence of a second or additional such feature or element.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein.

In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A neutral hybrid braided structure, comprising:
a first set of wires arranged in a first set of positions;
a second set of wires arranged in a second set of positions,
wherein the first set of wires and the second set of wires are braided together to form the neutral hybrid braided structure,
wherein each wire in the first set of wires has a first cross-sectional diameter, and wherein each wire in the second set of wires has a second cross-sectional diameter that is smaller than the first cross-sectional diameter;
wherein the first set of positions and the second set of positions form a neutral hybrid braid pattern;
wherein each wire of the first set of wires is positioned immediately adjacent at least one other wire of the first set of wires, and each wire of the second set of wires is positioned immediately adjacent at least one other wire of the second set of wires; and
wherein at four locations around a diameter of the braided structure at least three of the second set of wires are positioned consecutively.

2. The braided structure of claim 1, wherein each of the wires of the first set of wires and the second set of wires is made of a shape memory material.

3. The braided structure of claim 2, wherein the shape memory material comprises Nitinol.

4. The braided structure of claim 1, further comprising:
a plurality of CW high points, wherein the second set of wires cross over the first set of wires in a CW direction; and
a plurality of CCW high points, wherein the second set of wires cross over the first set of wires in a CCW direction.

5. The braided structure of claim 1, wherein the braided structure is configured to expand into an expanded configuration comprising a plurality of lobes.

6. The braided structure of claim 5, wherein a reduced diameter portion is disposed between adjacent lobes of the plurality of lobes in the expanded configuration.

7. A catheter assembly, comprising:
a catheter; and
a neutral hybrid braided structure disposable within a lumen of the catheter, the neutral hybrid braided structure comprising:
a first set of wires arranged in a first set of positions; and
a second set of wires arranged in a second set of positions;
wherein the first set of wires and the second set of wires are braided together to form the neutral hybrid braided structure;
wherein each wire in the first set of wires has a first cross-sectional diameter;
wherein each wire in the second set of wires has a second cross-sectional diameter that is smaller than the first cross-sectional diameter; and
wherein the first set of positions and the second set of positions form a neutral hybrid braid pattern;
wherein the catheter is configured to constrain the neutral hybrid braided structure in a radially collapsed configuration; and
wherein when the braided structure is not constrained by the catheter, the braided structure is configured to expand into an expanded configuration comprising a plurality of lobes.

8. The catheter assembly of claim 7, wherein each of the first set of wires is positioned immediately adjacent at least one other wire of the first set of wires, and each of the second set of wires is positioned immediately adjacent at least one other wire of the second set of wires; and
wherein at four locations around a diameter of the braided structure at least three of the second set of wires are positioned consecutively.

9. The catheter assembly of claim 7, wherein each of the wires of the first set of wires and the second set of wires is made of a shape memory material.

10. The catheter assembly of claim 7, wherein the shape memory material comprises Nitinol.

11. The catheter assembly of claim 7, further comprising:
a plurality of CW high points, wherein the second set of wires cross over the first set of wires in a CW direction; and
a plurality of CCW high points, wherein the second set of wires cross over the first set of wires in a CCW direction.

12. The catheter assembly of claim 7, wherein a reduced diameter portion is disposed between adjacent lobes of the plurality of lobes in the expanded configuration.

13. The catheter assembly of claim 7, wherein the braided structure is configured to be constrained within the lumen of the catheter, such that a plurality of CW high points of the braided structure and a plurality of CWW high points of the braided structure contact a wall of the lumen of the catheter.

14. The catheter assembly of claim 7, wherein the braided structure is configured to engage with a wall of the lumen of the catheter as the braided structure is displaced proximally or distally through the lumen of the catheter, such that a rotation of the braided structure is neutral.

15. A neutral hybrid braided structure, comprising:
a first set of wires arranged in a first set of positions;
a second set of wires arranged in a second set of positions, wherein the first set of wires and the second set of wires are braided together to form the neutral hybrid braided structure,
wherein each wire in the first set of wires has a first cross-sectional diameter, and wherein each wire in the second set of wires has a second cross-sectional diameter that is smaller than the first cross-sectional diameter;
wherein the first set of positions and the second set of positions form a neutral hybrid braid pattern;
wherein each wire of the first set of wires is positioned immediately adjacent at least one other wire of the first set of wires, and each wire of the second set of wires is positioned immediately adjacent at least one other wire of the second set of wires;
wherein at four locations around a diameter of the braided structure at least three of the second set of wires are positioned consecutively; and
wherein at two locations around the diameter of the braided structure at least four of the first set of wires are positioned consecutively.

\* \* \* \* \*